(12) United States Patent
Doubler et al.

(10) Patent No.: US 8,197,546 B2
(45) Date of Patent: Jun. 12, 2012

(54) CORPECTOMY IMPLANT

(75) Inventors: Robert L. Doubler, Monroe, MI (US); John E. Hammill, Sr., Maumee, OH (US)

(73) Assignee: Ortho Innovations, LLC, Palm Beach Gardens, FL (US)

( * ) Notice: Subject to any disclaimer, the term of this patent is extended or adjusted under 35 U.S.C. 154(b) by 674 days.

(21) Appl. No.: 12/268,698

(22) Filed: Nov. 11, 2008

(65) Prior Publication Data

US 2009/0138089 A1 May 28, 2009

Related U.S. Application Data

(60) Provisional application No. 60/990,535, filed on Nov. 27, 2007.

(51) Int. Cl.
*A61F 2/44* (2006.01)
(52) U.S. Cl. .................... 623/17.15; 606/279
(58) Field of Classification Search .................. 606/279; 623/17.11–17.16
See application file for complete search history.

(56) References Cited

U.S. PATENT DOCUMENTS

| | | | |
|---|---|---|---|
| 5,171,278 A | 12/1992 | Pisharodi | |
| 5,290,312 A | 3/1994 | Kojimoto et al. | |
| 6,176,881 B1 | 1/2001 | Schar et al. | |
| 6,200,348 B1 | 3/2001 | Biedermann et al. | |
| 6,419,705 B1 | 7/2002 | Erickson | |
| 6,524,341 B2 | 2/2003 | Lang et al. | |
| 6,730,088 B2 * | 5/2004 | Yeh | 606/247 |
| 6,866,682 B1 * | 3/2005 | An et al. | 623/17.15 |
| 7,029,498 B2 | 4/2006 | Boehm et al. | |
| 7,544,208 B1 * | 6/2009 | Mueller et al. | 623/17.15 |
| 7,674,296 B2 * | 3/2010 | Rhoda et al. | 623/17.15 |
| 8,062,366 B2 * | 11/2011 | Melkent | 623/17.11 |
| 2006/0004447 A1 | 1/2006 | Mastrorio et al. | |
| 2006/0058879 A1 * | 3/2006 | Metz-Stavenhagen | 623/17.15 |
| 2007/0255408 A1 | 11/2007 | Castleman et al. | |
| 2007/0255409 A1 * | 11/2007 | Dickson et al. | 623/17.11 |

* cited by examiner

*Primary Examiner* — Thomas C. Barrett
*Assistant Examiner* — Larry E Waggle, Jr.
(74) *Attorney, Agent, or Firm* — McHale & Slavin, P.A.

(57) ABSTRACT

The present invention describes an expandable vertebral implant and the method of use. The longitudinally expandable vertebral implant includes telescoping sections adapted for incremental expansion and ease of securement at any desired increment in situ, and constructed and arranged to engage opposing vertebrae. The corpectomy device is a distractible vertebral body replacement for the thoracic and lumbar spine. The device is cylindrical shaped having an inner and outer sleeve made adjustable by use of locking pads formed integral with the outer sleeve for use in engaging parallel circumferential locking grooves formed along the outer side surface of the inner sleeve.

15 Claims, 11 Drawing Sheets

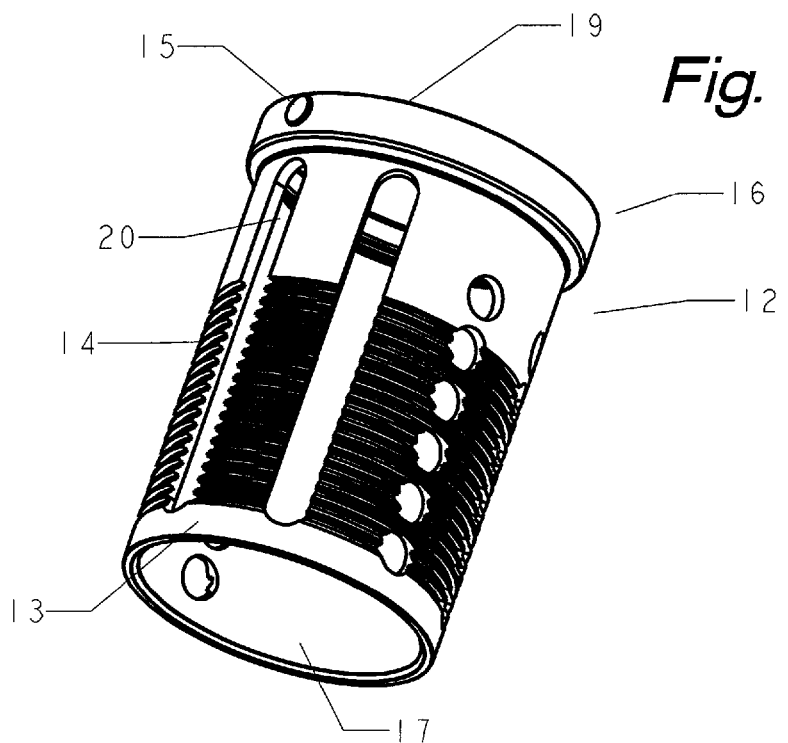
Fig. 2
Fig. 3
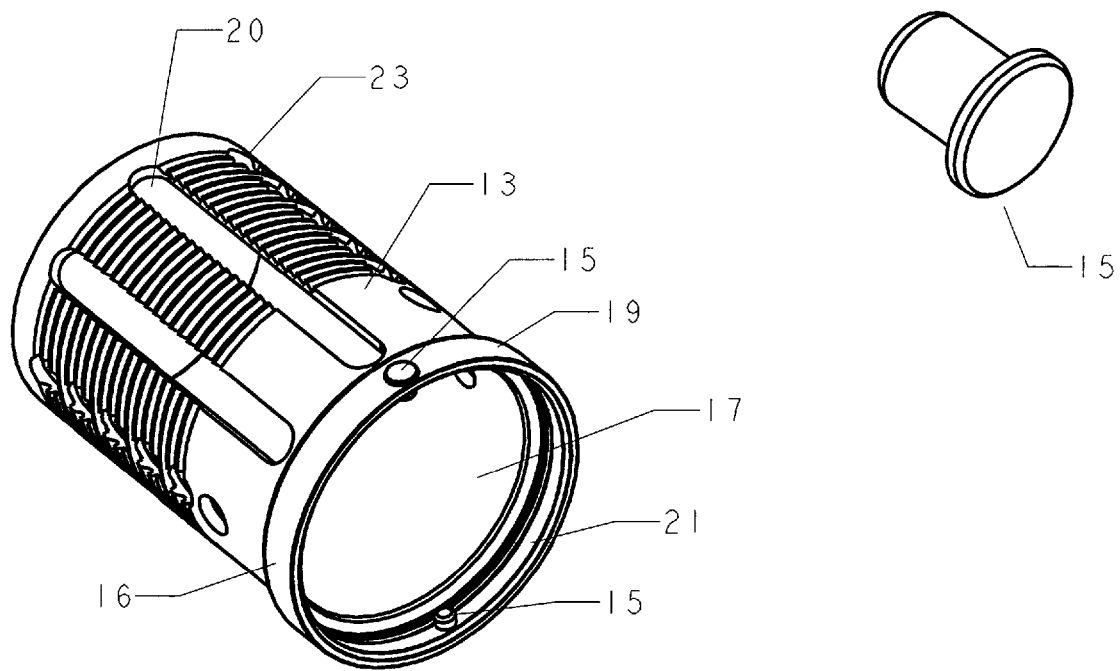
Fig. 4

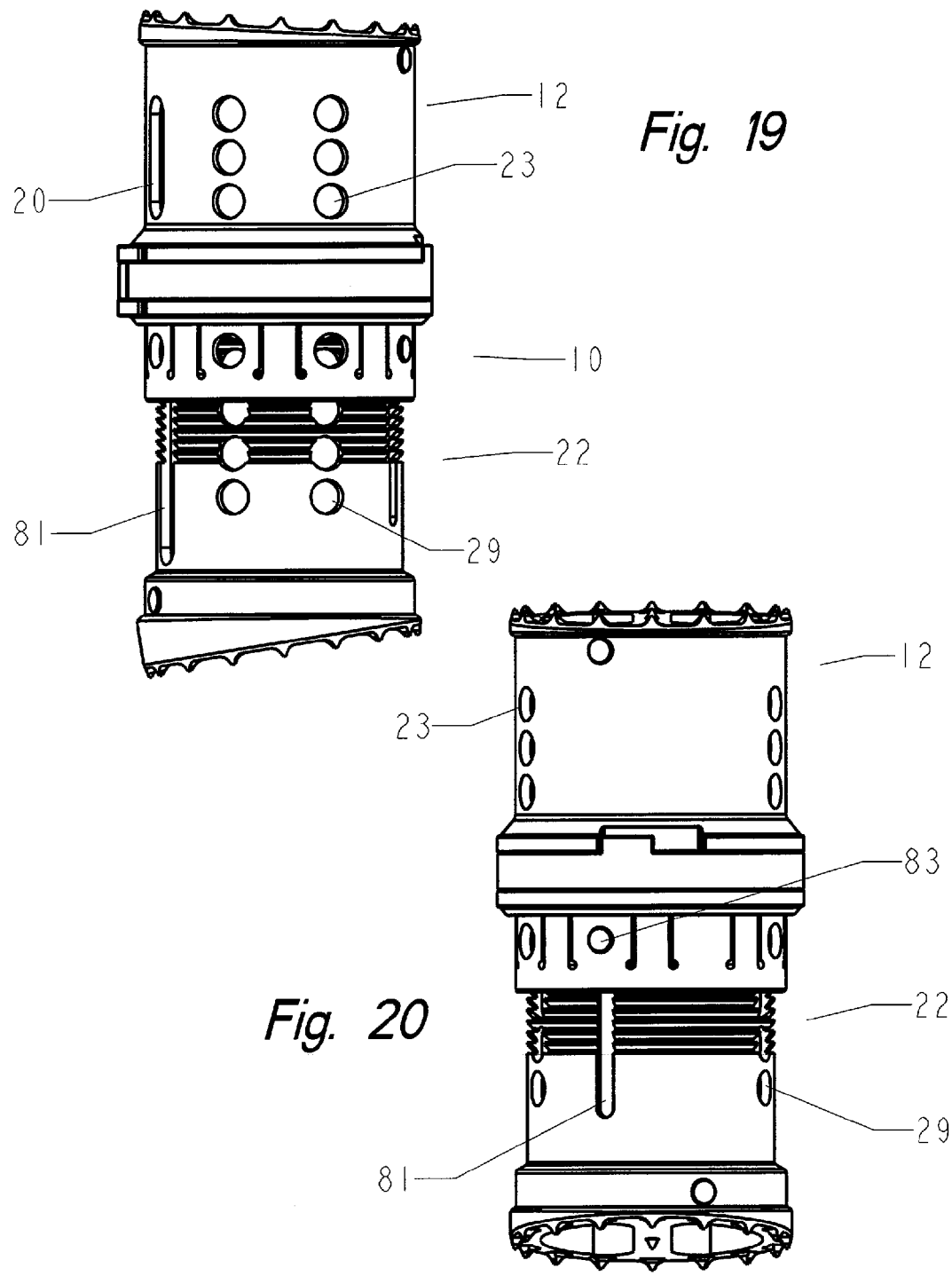

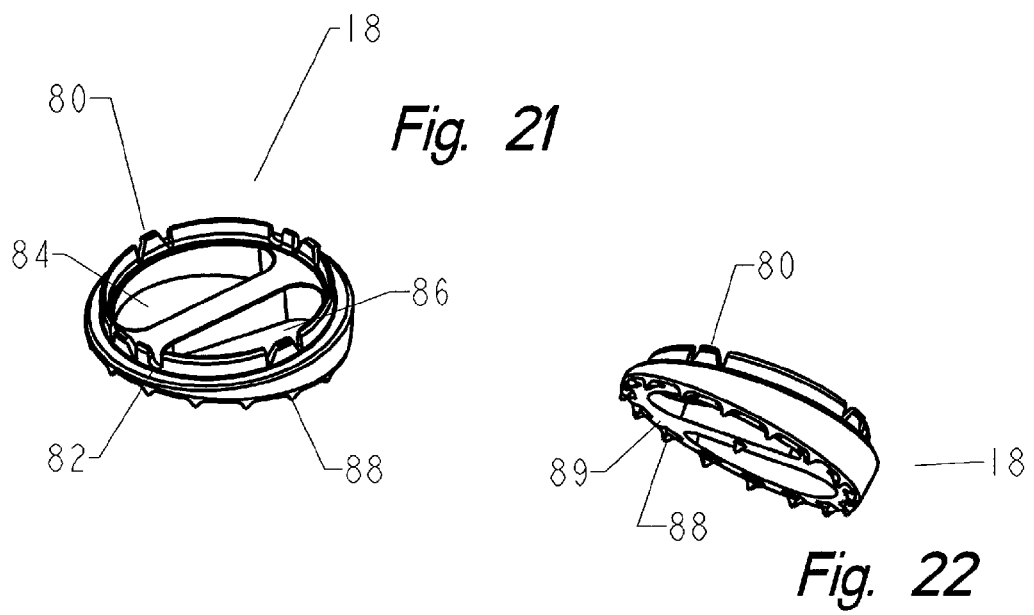
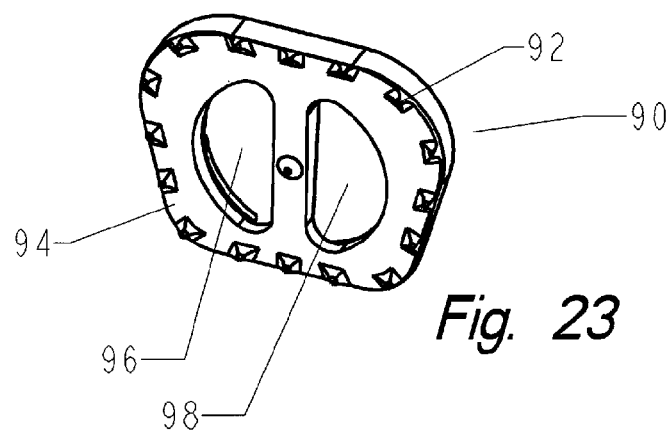
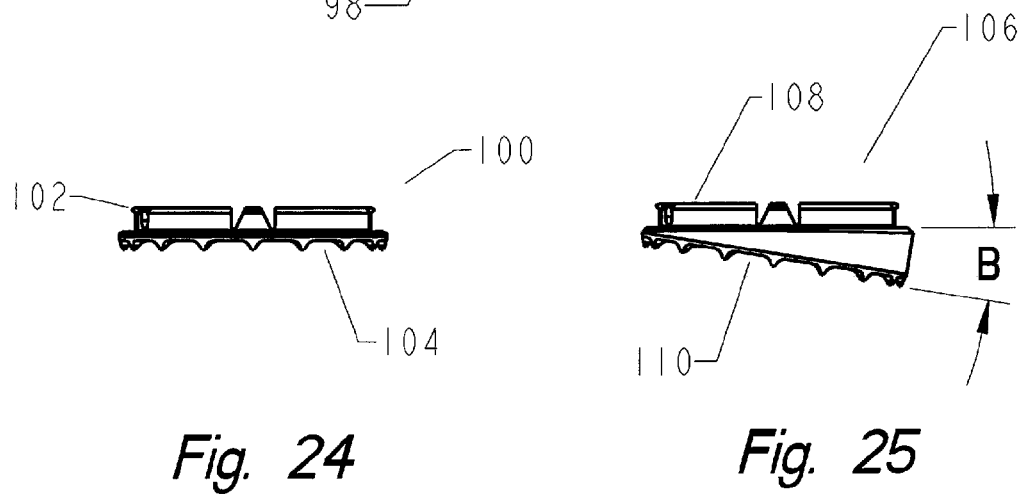

CORPECTOMY IMPLANT

PRIORITY CLAIM

This application is based upon U.S. Provisional Patent Application No. 60/990,535 filed Nov. 27, 2007, the contents of which are incorporated herein by reference.

FIELD OF THE INVENTION

The invention generally relates to vertebral body replacements and more particularly, to a distractible vertebral body replace for the thoracic and lumbar spine.

BACKGROUND OF THE INVENTION

The human vertebrae may be classified as the cervical, thoracic and lumbar sections. The vertebrae are separated by small cartilaginous cushions identified as intervertebral discs. Chronic back problems often manifest themselves due to a rupture or degeneration of these intervertebral discs either as a result of disease, injury or advanced age. When disc abnormalities occur, nerves within or adjacent to the spinal column may become inflamed or impinged resulting in the individual experiencing pain of varying degree and manifestation, diminished flexibility and reduced range of motion.

In order to reduce the pain associated with the movement of the intervertebral joint, surgical intervention is often indicated as a means to alleviate pressure upon the spinal cord while concomitantly stabilizing the associated vertebrae. This involves a surgical procedure to distract the disc and or vertebra, or portions thereof, and the insertion of bone fusing material into the cavity of the opposing vertebra. Corpectomy devices have been developed to help support the spine and maintain the normal spacing between opposing vertebrae. Some of these devices may be packed with fusing material to ensure solid bone growth between the two vertebrae.

Typically, corpectomy devices are pre-manufactured at various heights requiring that a cavity between opposing vertebrae be prepared and distracted to a dimension corresponding to the most suitably sized corpectomy device. The surgical procedure to prepare the implant site can be difficult and lengthy. Moreover, the procedure can increase risk of trauma to the tissues surrounding of the implant site.

Recently, distractible corpectomy devices that have been developed may be used as both a fusion device and/or a means for maintaining intervertebral spacing. Often these implants include a drive means that allows the corpectomy device to be expanded in situ to a size that corresponds to the cavity created when the damaged tissue is removed. The drive means typically includes devices such as gears, threaded rods, and the like, in mechanical engagement so as to expand or contract the device to a necessary distance between the vertebrae. Such constructions are complicated as they must necessarily comprise many moving parts, which likewise make them expensive to manufacture and more prone to failure. Moreover, when elongated to their expanded position, these devices often fail to provide a substantially enclosed cavity capable of retaining bone fusing material therein, which is often used to ensure fusion between the two vertebrae.

Although there are numerous patents directed to both artificial disk implants and expandable corpectomy devices, adapted for insertion and securement within the intervertebral space, the prior art nevertheless fails to teach an expandable corpectomy device which is capable of securely retaining bone growth/fusion materials therein, and which offers a means for simple incremental adjustment, thereby providing an individualized fit.

U.S. Pat. No. 5,171,278, to Pisharodi discloses an artificial disk implant and methods for implanting it, wherein the implant has a member for adapting, in size and shape, to an anatomical space between vertebrae and apparatus for expanding the member to conform to the space. Unlike the present invention, the design of this implant does not provide an internal cavity suitable for retention of fusing material to ensure solid bone growth between the two vertebrae.

U.S. Publication No. 2007/0255408 and 2007/0255409 disclose an expandable, implantable device to provide fixation between or among anatomical structures.

U.S. Pat. No. 6,524,341 discloses a vertebral bone prosthetic device comprising an interior body with an outer surface and a first coupling element thereon configured and dimensioned to be slidably received along a central axis by the exterior hollow body with a bore therein, and provided with an interior surface having a groove and an exterior surface. The device also comprises a fixation ring having inner having a second coupling element thereon and outer surfaces. The fixation ring is configured and dimensioned to be received within the groove of the exterior body for rotational movement about the central axis. Rotation of the fixation ring results in engagement of the first and second coupling elements to thereby prevent relative sliding movement between the interior and exterior bodies.

U.S. Pat. No. 6,176,881 discloses a device for replacing vertebral bones. The device includes an interior hollow body providing a catch mechanism on its outer surface and an exterior hollow body including a hole or bore extending along the central axis which can slide into each other coaxially along a central axis and can be moved in relation to one another in the direction of the central axis. The exterior hollow body also includes at least one elastic element that projects into the bore at its top end reducing the diameter of the bore so that the elastic element latches onto the catch mechanism of the interior hollow body, thereby fixing the length of the device in such a way that it is resistant to compression.

U.S. Pat. No. 6,200,348 discloses a spacer for insertion between two vertebrae having a variable axial length. The spacer comprises a first sleeve-shaped member and a second member which is slidably guided within the first member adjusting the overall length. The members face each other on an axially extending portion having ratchet notch means allowing engagement for displacement to a desired overall length.

U.S. Pat. No. 5,290,312 discloses a prosthetic vertebra having a two shaped components, the second being marginally smaller than the first. The second component accordingly positioned partially axially within the first component allowing movement so that the overall length of the prosthetic vertebra can be established by appropriately moving the second component within the first. A set screw is threadably engageable with the first component and can be tightened against the second component to hold the components axially stationary relative to each other.

U.S. Pat. No. 6,419,705 to Erickson is directed to expandable bone fusion devices and methods of use. In general, a fusion device according to the invention includes a first member and a second member which can be deployed and locked into an expanded configuration to stabilize the adjacent bone during fusion thereof.

U.S. Pat. No. 6,866,682 to An et al., describes a corpectomy device with an inner member telescopingly disposed in an outer member so that the inner member is movable in an axial direction. The inner and outer members are hollow, defining a chamber, and include apertures in communication with the chamber. A locking clip engages the inner and outer members to fix the position of the inner member with respect to the outer member. The longitudinal dimension of the device is adjustable by distracting the inner member so that the inner member extends from the outer member, and subsequently moving the locking clip from an unlocked position to a locked position. Again, unlike the present invention, the design of this implant includes multiple slots which, in the extended position, fail to provide an internal cavity capable of preventing fusing material therein from leaking, thereby resulting in impaired fusion at the insertion site. Moreover, the device requires the use of at least two separate locking means, and the device must be rotated and a set screw inserted therein to secure the locking clip at the desired longitudinal distance. This construction is problematic in that rotation of the implant in situ is difficult.

U.S. Pat. No. 7,029,498 to Boehm et al., discloses a height-variable vertebral body implant having a first, essentially U-shaped or C-shaped cage, and vertebral support surfaces formed on the first cage. The first cage is an inner cage, which is embraced and guided in a telescopic manner by a second, outer U-shaped or C-shaped cage. Further, legs of the inner and the outer cage are aligned such that a continuous lateral opening is obtained, and the inner and the outer cages are mutually fixed in a predetermined final position. The inner cage includes a longitudinally extending elongated hole having a unilateral toothing. In cooperation with an instrument including a complementary toothing, a relative movement and adjustment may be effected between the cages. In addition, a thread bore is formed in the outer cage in a position below the area of the elongated hole to fix a desired adjustment position. Again, this type of construction is undesirable given that it requires in situ alignment of a plurality of parts in constrained and difficult circumstances.

U.S. Patent Pub. No. 2006/0004447 to Mastrorio et al. is drawn to a height-adjustable device suitable for insertion between posterior spinal processes that allow the surgeon to post-operatively adjust the height of the implant. This reference is typical of devices which are fraught with mechanical deficiencies owing to their inclusion of a complicated drive means to separate the ends of the implant in communication with the vertebrae.

SYNTHES® Spine has an expandable vertebral body replacement device entitled the SYNEX™ System. The device has parallel grooves that operate in a ratchet assembly with each step producing about 2.5 mm of distraction.

The aforementioned prior art disclose expandable vertebral implants constructed such that the majority of forces (contracting) from the tissue structures surrounding the joint are placed upon a single gear mechanism. This stress can eventually lead to cavitation of the device and possible damage to the vertebrae itself.

What is lacking in the prior art is an expandable corpectomy device which offers a simple and easily operable means for effecting incremental expansion/contraction of the device and provides a secure closure effective for maintaining the device at a pre-selected degree of expansion/contraction.

SUMMARY OF THE INVENTION

The instant invention is a corpectomy device in the form of a distractible vertebral body replacement for the thoracic and lumbar spine. The corpectomy device is constructed and arranged to fit within the intervertebral distracted channel and provides a defined cavity for bone growth/fusion material. The corpectomy device of the instant invention is cylindrical shaped having an inner and outer sleeve made adjustable by use of locking pads formed integral with the outer sleeve for use in engaging parallel circumferential locking grooves formed along the outer side surface of the inner sleeve.

It is an objective of the instant invention to provide a pre-assembled cylindrical shaped corpectomy device that is available in various diameters and lengths.

Still another objective of the invention is to provide a corpectomy device that is expandable having a locking mechanism capable for maintaining the desired length and cause even load distribution around the cylindrical sleeves.

Another objective of the invention is to provide a corpectomy device that may be distractible in situ.

It is a further objective of the instant invention to provide an expandable corpectomy which includes means effective for enabling bone fusion after being implanted within the patient, such means illustratively represented as slots, or the like, but eliminates the slots on the posterior side to prevent migration bone graft.

Yet another objective of the instant invention is to provide vertebra engagable endplates which may be constructed and arranged to accommodate various angular displacements of the cavity endpoints, and are effective to restore the normal curvature of the spine after the corpectomy device is installed.

Still a further objective of the invention is to teach a quick locking feature upon length adjustment.

Still another objective of the invention is to provide a corpectomy device having a solid side wall to prevent migration bone graft along the posterior side.

Another objective of the invention is to provide a corpectomy device having end plates with a large surface area for load bearing.

Yet still another objective of the invention is to provide a corpectomy device having endplates with an open end design to maximize area for bone-to-bone contact.

Another objective of the invention is to provide a corpectomy device having modular endplates that provide a variety of angles for restoring the contour of the spine, the endplates being interchangeable with snap-on assembly with orientation.

Yet still another objective of the invention is to provide a corpectomy device having endplates that may include spikes for stabilization and to resist rotation and/or migration.

These and other objectives and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

FIG. 2 is a perspective view of the inner sleeve sub assembly;

FIG. 3 is a perspective view of a pin used for endplate orientation and guiding;

FIG. 4 is a lower perspective view of FIG. 2;

FIG. 19 is a side view of the device in full expansion;

FIG. 20 is a back posterior view of the device in full expansion;

FIG. 21 is a top perspective view of an endplate;

FIG. 22 is a bottom perspective view of an endplate;

FIG. 23 is a bottom perspective view of an oblong shaped endplate;

FIG. 24 is a side view of an flat endplate; and

FIG. 25 is a side view of an angled endplate.

DETAILED DESCRIPTION OF THE INVENTION

Figure 1:
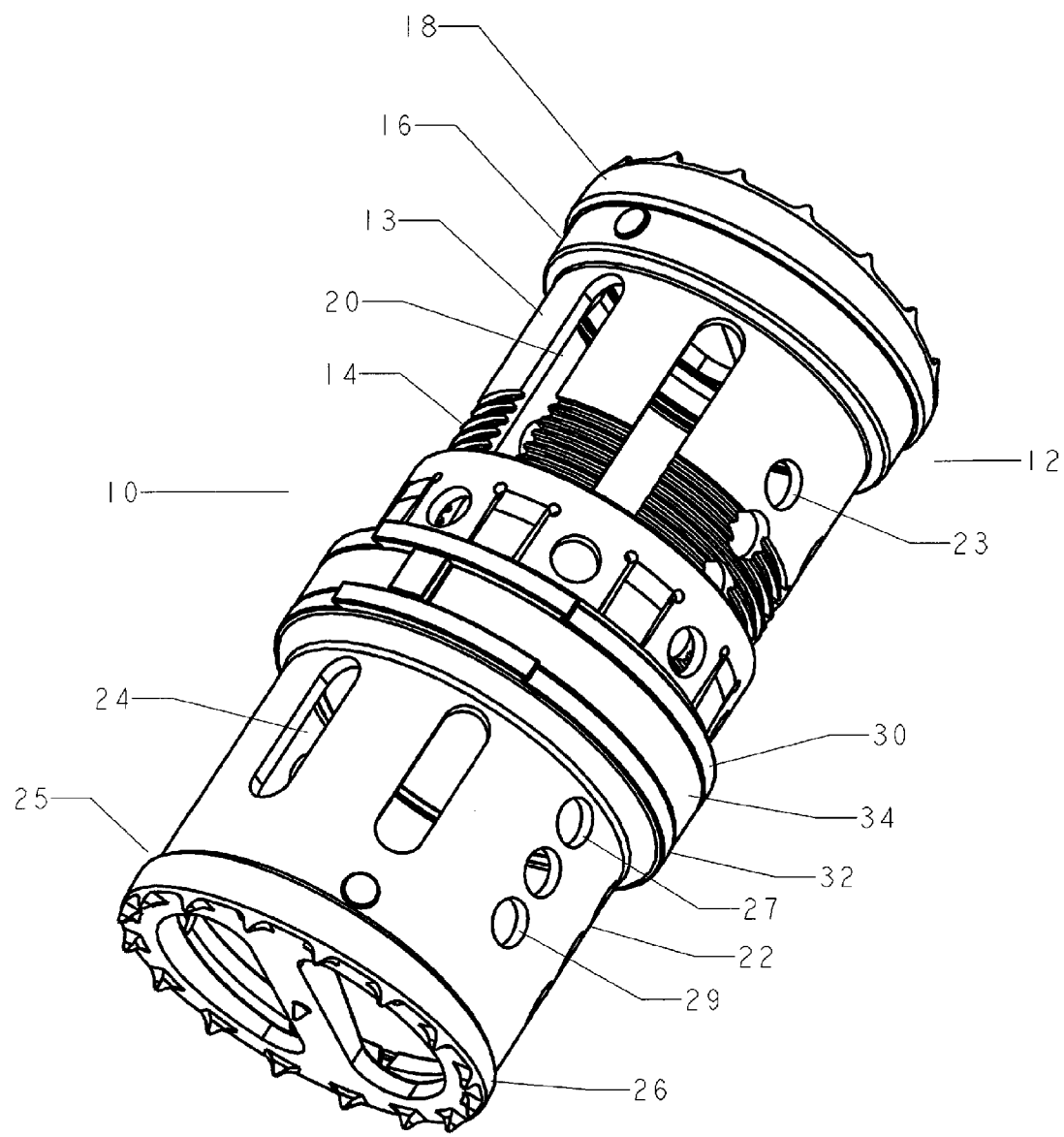
FIG. 1 is a perspective view of the corpectomy implant.

Now referring to FIG. 1, set forth is the corpectomy device (10) of the instant invention. The device consists of a cylindrical shaped inner sleeve (12) having a side wall (13) with parallel circumferential locking grooves (14). The sleeve is further defined by a base (16) and end plate (18). The side wall (13) of the inner sleeve includes a plurality of elongated slots (20) for maximum bone growth which is positioned perpendicular to the locking grooves (14) and apertures (23) that allows for minimal bone growth. The inner sleeve is operatively associated with a cylindrical shaped outer sleeve (22) having a plurality of slots (24) coaxial aligned with the slots of the inner sleeve and/or the use of apertures (23).

End plate (26) is positioned along end (25) of the outer sleeve (22). The side wall (27) of the outer sleeve includes a first guide ring (30) that is preferable made a part of the sleeve component, a second guide ring (32) and a locking ring (34). Elongated slots (24) allow for maximum bone growth transfer and apertures (29) allow for minimal bone growth transfer. It should be noted that these rings are circumferential for use in engagement of the locking grooves (14) around the circumference of the device.

Now referring FIG. 2 and FIG. 4, set forth is the inner sleeve (12) depicting the parallel circumferential locking grooves (14) separated along the side wall (13) by slots (20) and apertures (23). It should be noted that the posterior side wall as depicted by numeral (17) is lacking the use of slots so as to prevent bone graph migration toward the spinal cord. Further, the reduction of the slots (20) to the apertures (23) further limits bone graph migration when approaching the spinal cord. The slots (20) allow bone graft material to be placed within the inner side walls of the sleeves, which forms a cavity, which allows growth between existing bone and the implant providing further stabilization. The base (16) includes a raised outer edge (19) so as to form a lip (21) allowing acceptance of an end plate. Pin (15), further shown in FIG. 3, operates as an endplate orientation pin for use in maintaining the endplate positioned within the lip in a predetermined orientation.

Figure 5:
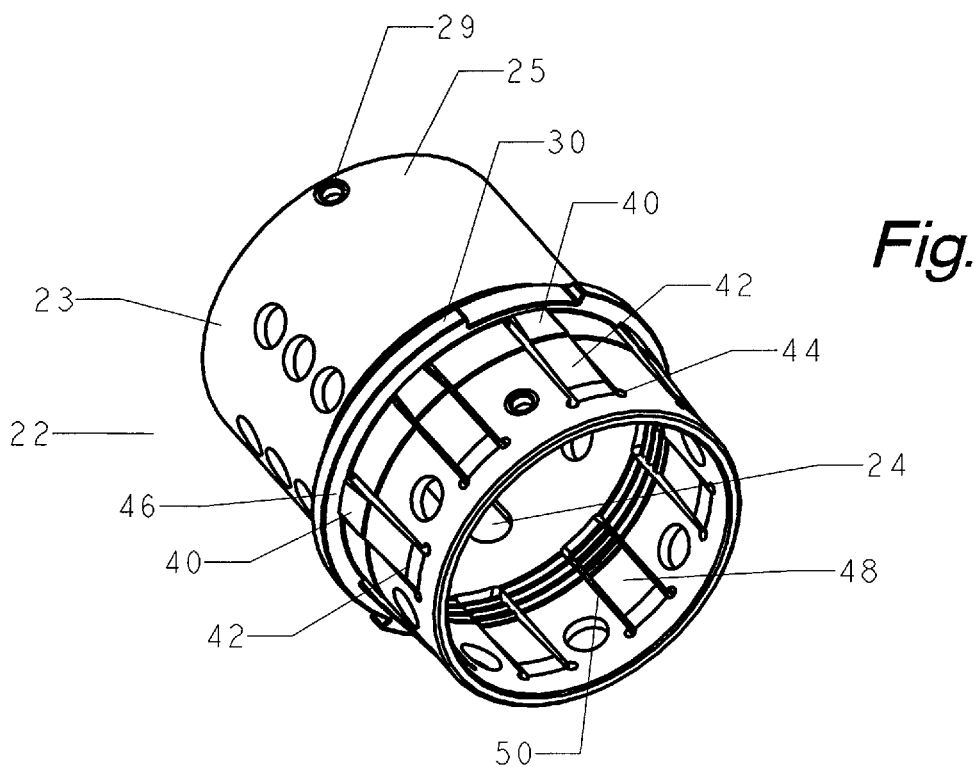
FIG. 5 is a perspective view of the outer sleeve sub assembly with a guide ring.

FIG. 5 depicts the outer sleeve (22) having a cylindrical shaped side wall (23). One section of the sidewall, depicted by numeral (25), provides positional alignment with the spine wherein the solid side wall prevents posterior bone graph migration. The side wall (23) opposite of sidewall (25) includes slots (24) so as to allow bone graft migration and apertures (23) positioned between the slots (24) and sidewall (25). The outer sleeve includes a plurality of locking pads as depicted by numeral (40) located about the circumference of the outer sleeve (22) having a bottom portion defined by relief points (44) at the base (42) with slots extending to the top (46) allowing movement of the locking pads between an unlocked position to a locked position, as further shown later, wherein the inner side surface (48) of the locking pads (40) include engagement teeth (50). Aperture (29) is receptive to insertion of pin (15) for use in alignment of the outer sleeve endplate, not shown.

Figure 6:
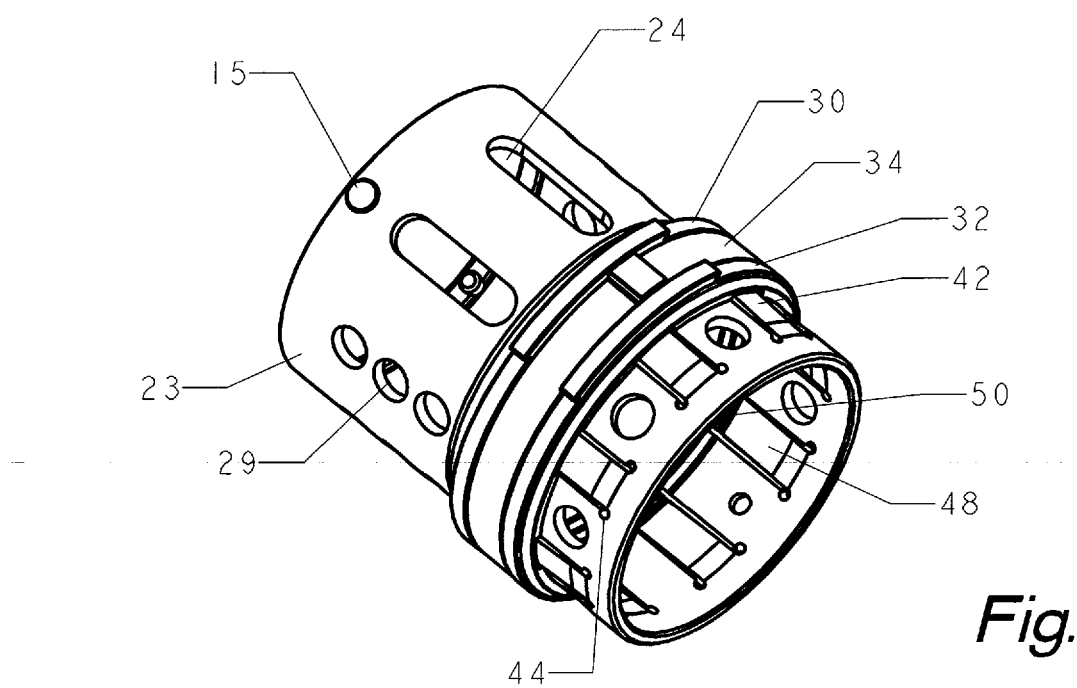
FIG. 6 is the outer sleeve assembly of FIG. 5 including a locking ring.

Depicted in FIG. 6 is the outer sleeve (22) shown with first and second circumferential guide rings (30 & 32) with a circumferential locking ring (34) positioned therebetween. The rotation of the locking ring (34) is used to force the teeth (50) into an engagement position which will interface with the parallel locking grooves (14) of the inner sleeve (12) as shown in FIG. 1. Placement of the device in the body is desirable with the maximum amount of bone growth material having exposure through the elongated slots (24) and a minimal amount of bone growth material having exposure through the apertures (29). No openings are positioned along the posterior side.

Figure 7:
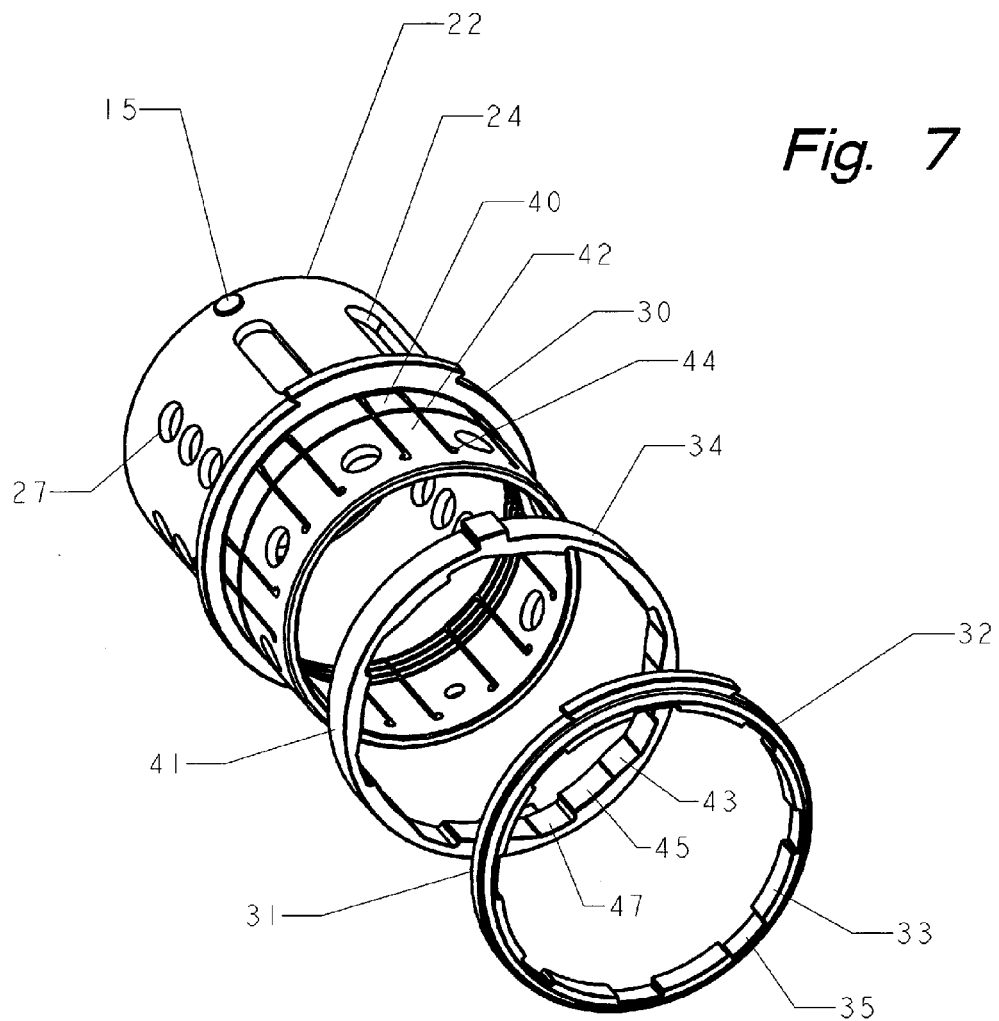
FIG. 7 is an exploded view of the outer sleeve assembly.

FIG. 7 depicts the guide ring (30) attached to the outer sleeve 22 along an end of locking pads (40). It should be noted that guide ring (30) may be formed integral to the sleeve, welded to the sleeve, or frictional engaged. The base (42) of the locking pads is biased in an outward position. Guide (30) and guide ring (32) are each formed from a single contiguous ring. Using guide ring (32) for depiction, the ring has an outer wall (31) and an inner wall (33) with a plurality of locking pad reliefs (35) for overlying of the locking pads. The locking ring (34) has an outer surface (41) and an inner surface having a locking pad relief (47), a transitional ramp (42), and a pad locking section (45). In operation, the locking ring (34) is rotated so as to allow pad reliefs (47) to move from a non-engaged position in respect to the locking pads (40) to an engaged position wherein locking pads (40) are depressed by pad locking member (45). Transitional ramp surface (43) is strategically located to allow movement of the locking ring from placement of the lock pads within the locking pad relief sections (47) to the pad locking member (45) thereby forcing the locking pad into a position engaging the locking grooves. The guide rings (30 & 32) are stationary and the locking ring (34) is allowed to rotate in relation thereto. The locked position causing the interlocking of parallel grooves between the locking pads on the outer sleeve and the circumferential locking grooves on the inner sleeve.

Figure 8:
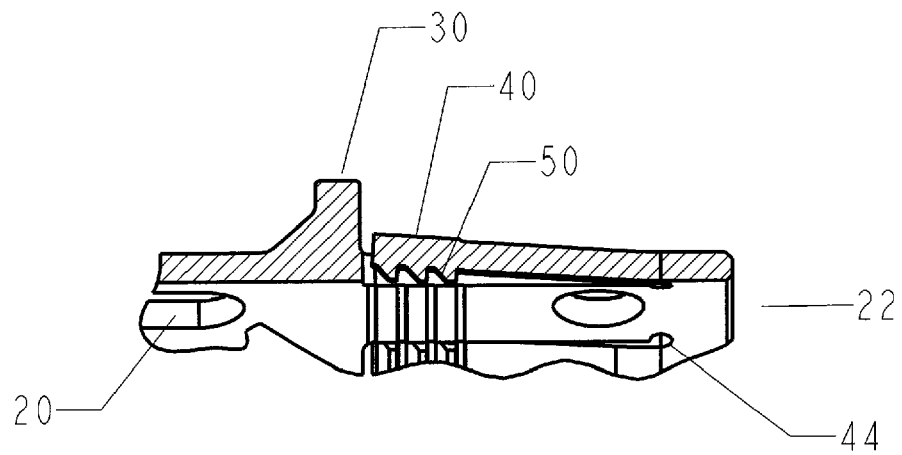
FIG. 8 is a cross sectional view depicting a locking pads and locking grooves.

FIG. 8 depicts the locking pad (40) of the outer sleeve (22) in a cross sectional side view. The locking pad (40) has engagement teeth (50) of a pitch that engages the locking grooves of the inner sleeve, the pitch allowing for each of expanding the length between the inner and outer sleeve with corresponding ramps, while the locking position provides a flat edge of the locking pad to a flat edge of the locking groove for positive positioning. Vertical column lock is achieved by mechanical interlocking of parallel grooves.

Figure 9:
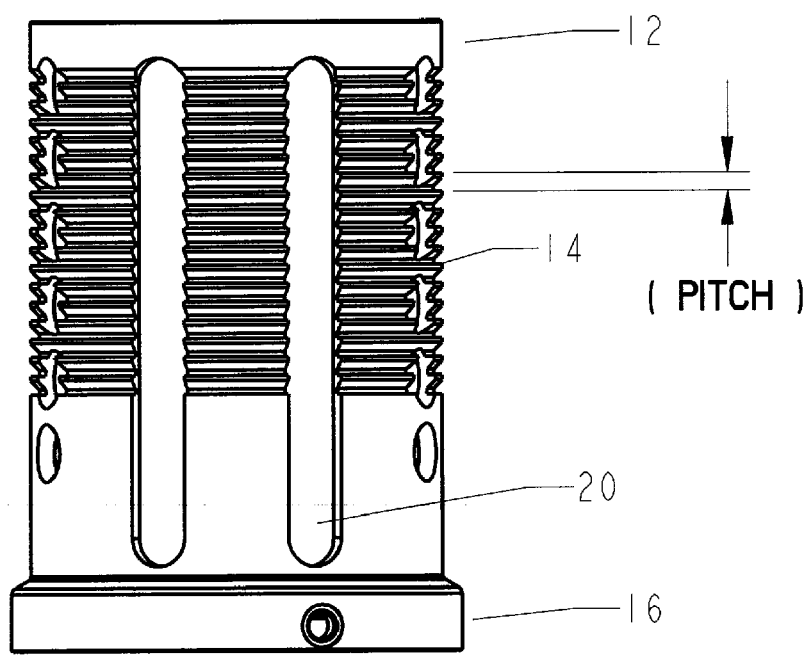
FIG. 9 is a side view of the inner sleeve depicting the pitch of the locking threads.

FIG. 9 depicts the inner sleeve (12) having a base (16), slots (20) and parallel circumferential locking grooves (14). As depicted by the pitch (Pitch), the parallel locking grooves are not threads and do not permit for the rotational increasing or decreasing of the height of the assembly. The parallel grooves with equal distant pitch provides a constant and predictable support across the entire bearing surface of the groove so as to eliminate side loading typical of a threaded or ratchet type design.

Figure 10:
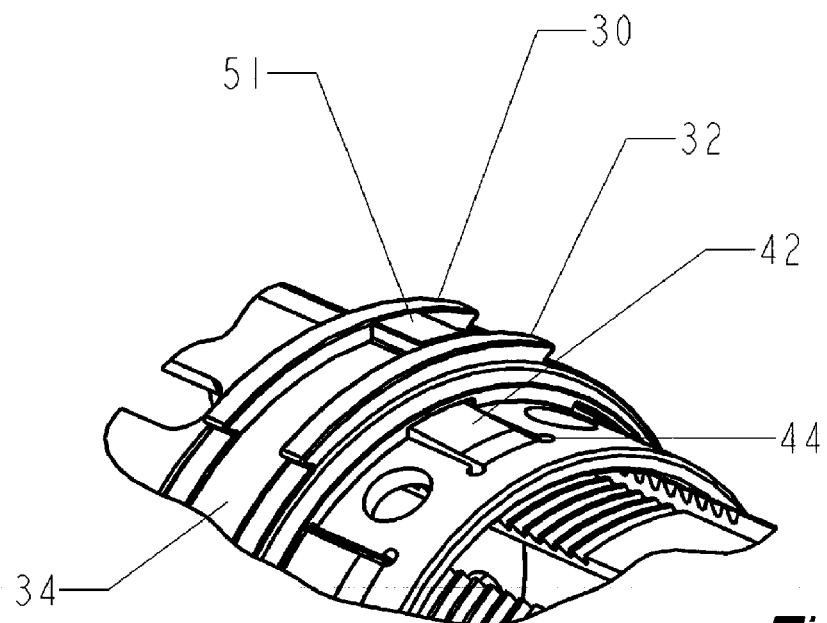
FIG. 10 is a partial perspective view of the locking ring in a disengaged position.

FIG. 10 depicts the first guide and second guide (30 and 32) in position with rotation of the locking ring (34) in a non-engaged position. Tab (51) is used to indicate the non-engagement position and may include indicia such as text markings. Tab (51) is illustrated in the non-engaged position where the locking pads base (42) can be viewed in a raised position with relief points (44) allowing the locking pad to be manufactured to maintain biased raised position.

Figure 11:
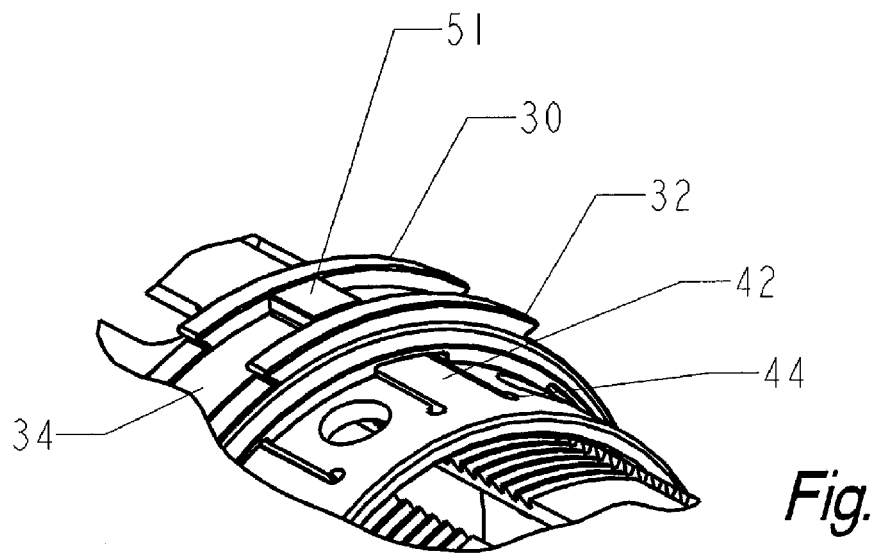
FIG. 11 is a partial perspective view of the locking ring in an engaged position.

FIG. 11 depicts the first and second guide rings (30 and 32) in adjustment with locking ring (34) depicted in a position that indicates a full and positive lock between the outer sleeve locking pads and parallel grooves of the inner sleeve. Tab (51) can be seen in a positioned rotated counterclockwise with the locking pads base (42) now placed in an engaged position with relief point (44) allowing the locking pad to freely bend in response to the movement of the tab (51).

Figure 12:
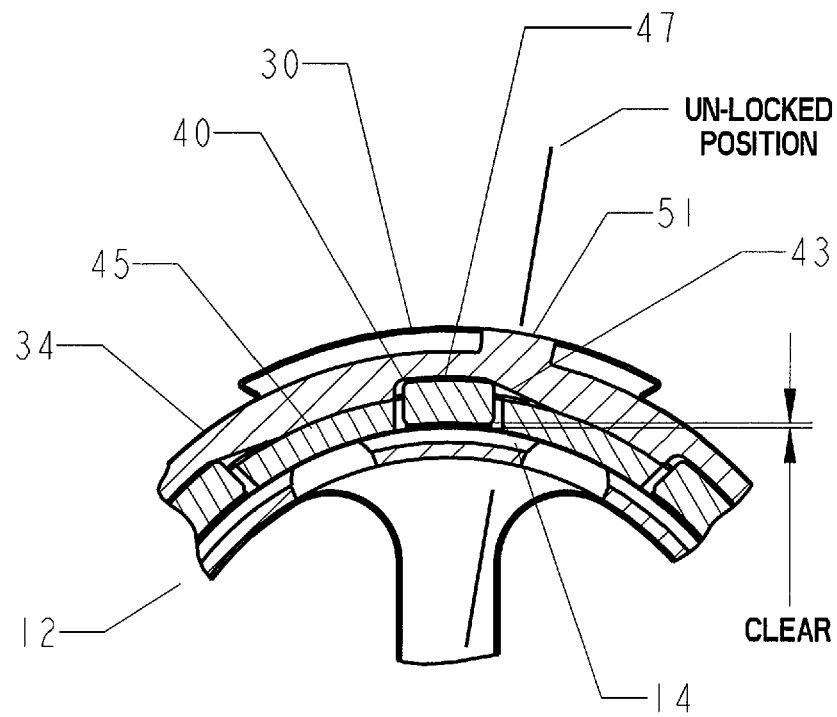
FIG. 12 is a cross sectional top view of the locking ring disengaged.
Figure 13:
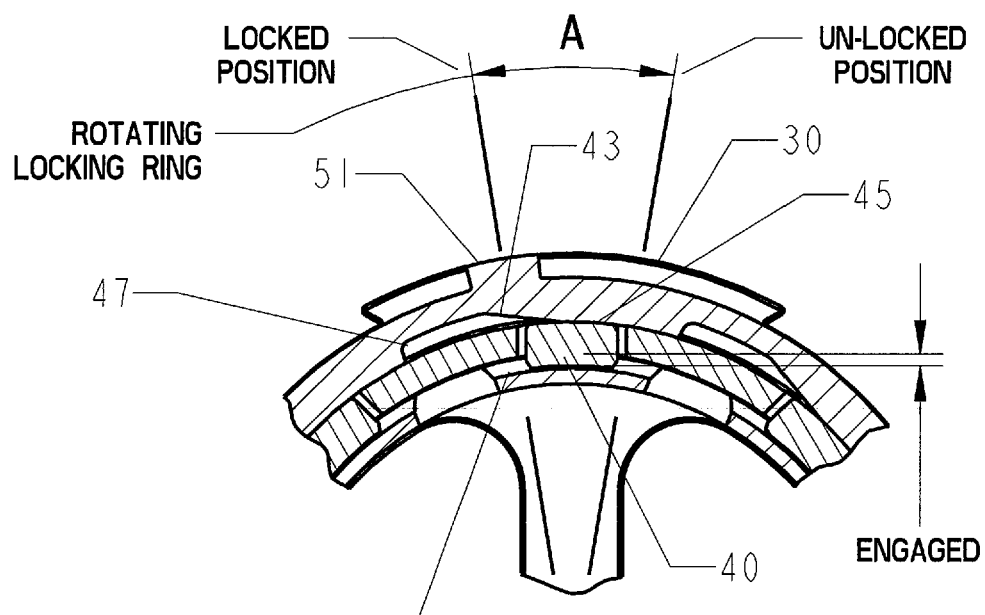
FIG. 13 is a cross sectional top view of the locking ring engaged.

FIG. 12 is a cross sectional view illustrating the locking ring (34) with tab (51) in an un-locked position in relation to guide ring (30) causing locking pad (40) to disengage locking groove (14) of the inner sleeve (12). The locking pad (40) is situated in the locking pad relief (47) with the transitional ramp (43) and pad locking section (45) depicted to the right.

Figure 15:
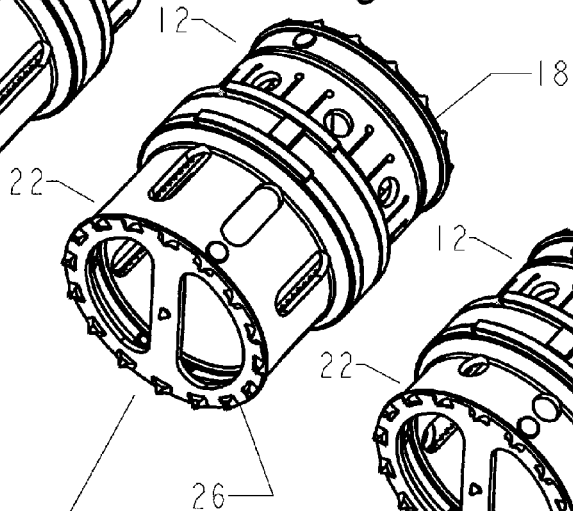

FIG. 15 illustrates the locking ring rotated in relation to the guide ring (30) wherein the tab (51) is now moved from an un-locked position (FIG. 12) to a locked position, the amount of clockwise rotation depicted on the drawing by distance (A). It should be noted that by use of the circumferential ring, it is not possible for rotation of the locking ring to occur unless alignment has taken place between the locking pads of the outer sleeve and the parallel grooves of the inner sleeve. Guide pins, not shown, prevent the inner sleeve from rotating in respect to the outer sleeve wherein the only rotation that may occur is with the locking ring (34). In operation, the locking ring (34) is rotated so as to allow pad locking member (45) to move from a non-engaged position in respect to the locking pads (40) to an engaged position wherein locking pads (40) are depressed by pad locking member (45). Transitional ramp surface (43) is strategically located to allow movement of the locking ring from placement of the lock pads within the locking pad relief sections (47) to the pad locking member (45) thereby forcing the locking pad (40) into a position engaging the locking grooves (14).

Figure 14:
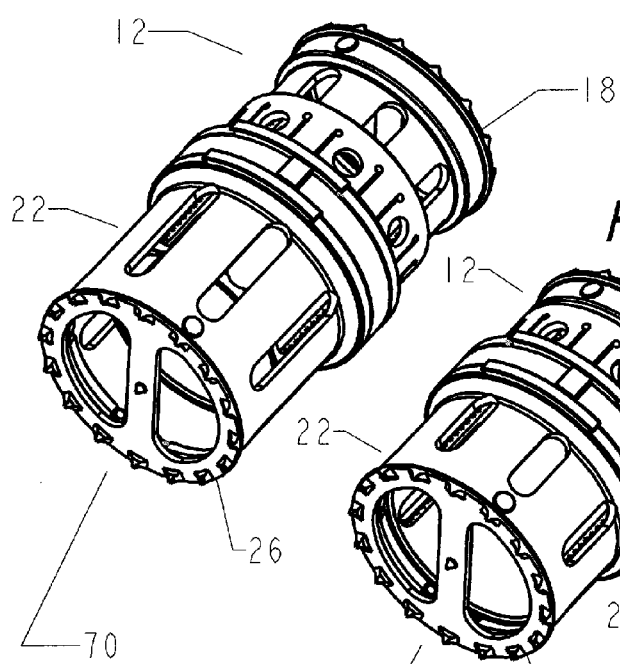
FIG. 14-16 are perspective views of various sized corpectomy implants.
Figure 16:
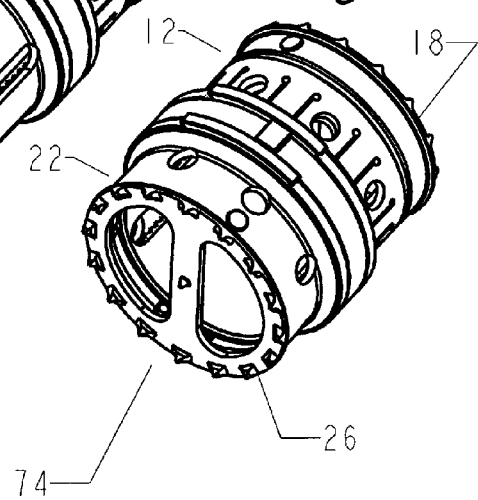

Now referring to FIGS. 14-16, set forth is an example of various distractible vertebral body replacements. So as to illustrate various sizes, FIG. 14 depicts a 22 mm diameter column 70 with a size that allows for an 18 mm range having a minimum required space of 42 mm and a maximum extension of 60 mm. FIG. 15 depicts a 12 mm diameter column 72 with a size that allows for a 12 mm range having a minimum required space of 30 mm and a maximum extension of 42 mm. FIG. 16 depicts a 22 mm diameter column 74 with a size that allows for a 6 mm range having a minimum required space of 24 mm and a maximum extension of 30 mm. Endplates are available in a selection of angles, both lordotic and kyphotic.

Figures 17, 18:
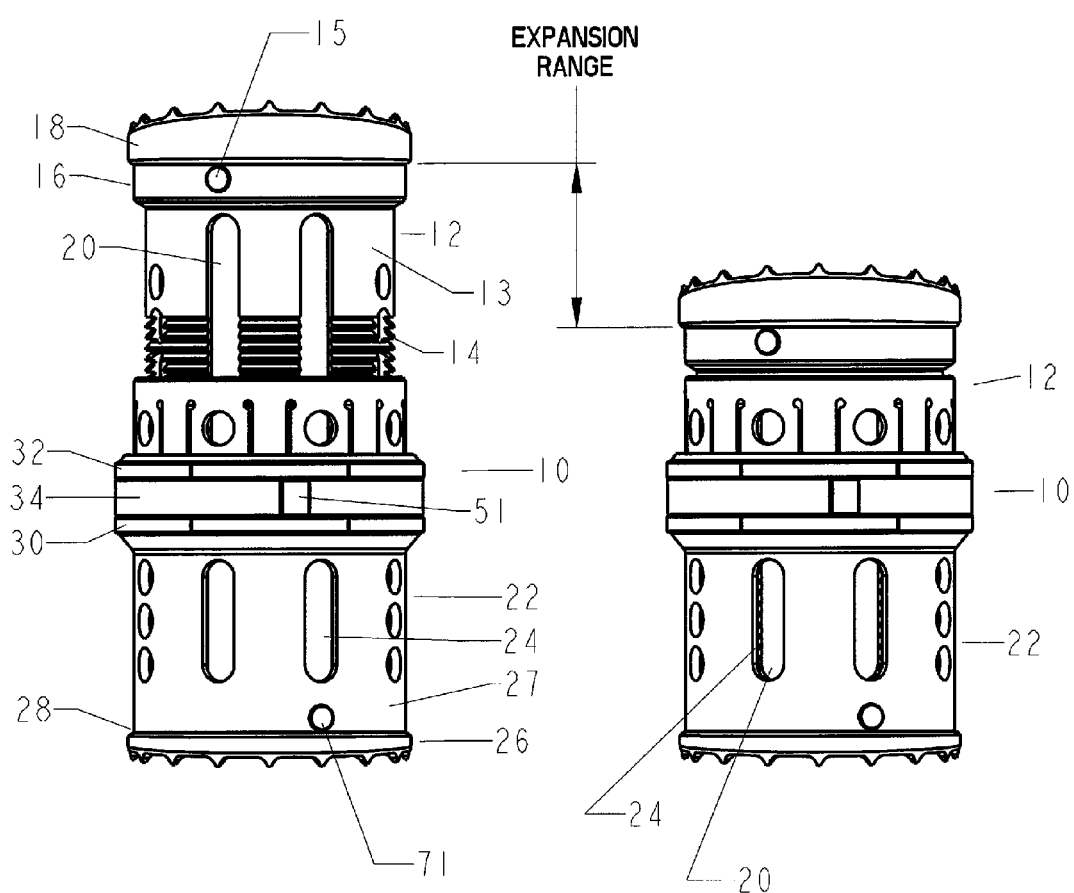
FIG. 17 is a front view of the device in full expansion.
FIG. 18 is a front view of the device without expansion.

FIG. 17 depicts a lateral view of the device (10) illustrating the cylindrical shaped inner sleeve (12) having a side wall (13) with parallel circumferential locking grooves (14). The sleeve is further defined by a base (16) and end plate (18). The side wall (13) of the inner sleeve includes a plurality of elongated slots (20) positioned perpendicular to the locking grooves (14). The inner sleeve is operatively associated with a cylindrical shaped outer sleeve (22) having a plurality of slots (24) coaxial aligned with the slots (20) of the inner sleeve. End plate (26) is positioned along end (28) of the outer sleeve (22). The side wall (27) of the outer sleeve includes first guide ring (30), second guide ring (32) and a locking ring (34). It should be noted that these rings are circumferential for use in engagement of the locking grooves (14) around the circumference of the device. Pin (15) positions the endplate (18) in a predetermined alignment position in respect to the inner sleeve. Pin (71) positions the endplate (26) in a predetermined alignment position in respect to the outer sleeve. FIG. 18 depicts the expansion range of the device (10) as compared to FIG. 17 wherein the cylindrical shaped inner sleeve (12) is drawn within the outer sleeve (22). It should be noted that elongated slots (20) and (24) remain aligned allowing for maximum bone growth transfer whether in an expanded position or in the contract position.

FIG. 19 depicts a side view of the device (10) having apertures (23) in the outer sleeve (12) and apertures (29) in the inner sleeve. FIG. 20 depicts a posterior side wall of the implant device which lacks slots as to prevent bone migration toward the spinal cord. A narrow slot 81 can be located on the inner sleeve 22 for engagement with an alignment pin 83 for maintaining the sleeves in alignment for proper opening widths of the slots and apertures.

FIGS. 21 and 22 depict a circular shaped endplate (18) having attachment snap-in fingers (80) allowing for secure positioning into the base of either the inner or outer sleeve. Orientation slot (82) provides directional positioning in relation to the guide pin. The endplate include large apertures (84) and (86) to permit maximum bone growth at the surface. The modular endplate have a snap-in-place configuration via resilient snap-in fingers (80) work in conjunction with the orientation features. The endplate can be in most any angles in both lordotic and kyphotic curves. Spikes (88) may be included along the outer surface (89) of the endplate to provide secure positioning against the bone. FIG. 23 depicts an oblong endplate (90) to illustrate the interchangeability of the endcaps with most any shape as needed for installation due to a particular configuration. The endplate (90) can include the use of spikes (92) on the outer surface (94). Large apertures (96) and (98) permit optimum bone growth along the surface.

FIG. 24 depicts a side view of an endplate (100) having a 0 degree angle between the snap-in portion (102) and engagement surface (104). FIG. 25 depicts an endplate (106) having a 9 degree angle B between the snap-in portion (108) and engagement surface 110. The endplates can be made in any size angle such as increment angles of 3 degrees.

Detailed embodiments of the instant invention are disclosed herein, however, it is to be understood that the disclosed embodiments are merely exemplary of the invention, which may be embodied in various forms. Therefore, specific functional and structural details disclosed herein are not to be interpreted as limiting, but merely as a basis for the claims and as a representation basis for teaching one skilled in the art to variously employ the present invention in virtually any appropriately detailed structure.

All patents and publications mentioned in this specification are indicative of the levels of those skilled in the art to which the invention pertains. All patents and publications are herein incorporated by reference to the same extent as if each individual publication was specifically and individually indicated to be incorporated by reference. It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A corpectomy device comprising an inner cylindrical sleeve having a first and second end and cylindrical shaped side wall there between and an outer cylindrical sleeve having a first and second end and a cylindrical shaped side wall there between;
    the external diameter of the inner sleeve being less than the inner diameter of the outer sleeve; whereby the first end of said inner cylindrical sleeve is telescopically received within the first end of the outer cylindrical sleeve;
    said cylindrical side wall on said inner sleeve including a plurality of parallel circumferential locking grooves on an external surface of said cylindrical side wall;
    said side wall on said outer sleeve including a plurality of locking pads located about the circumference of said outer sleeve, each of said locking pads configured to engage at least one circumferential groove on the cylindrical side wall of said inner sleeve;
    said outer cylindrical sleeve including an annular circumferential locking ring positioned on the outer cylindrical sleeve with a first guide ring, said first guide ring is a one piece ring having an outer wall and an inner wall, said inner wall is smooth in circumference, said annular circumferential locking ring is positioned between said first guide ring and a second guide ring, wherein the annular circumferential locking ring and the first and second guide rings each include tabs which provide a visual indication that the locking ring is either in the first or second position, and is mounted for rotary movement with respect to said outer cylindrical sleeve, and is rotatable between two positions; wherein a first position disengages the locking pads from at least one of the circumferential grooves and allows telescoping motion between the inner cylindrical sleeve and the outer cylindrical sleeve wherein a second position engages at least one of said circumferential grooves and locks the inner and outer cylindrical sleeves in a fixed telescopic relationship.

2. The corpectomy device of claim 1, wherein the cylindrical shaped side wall of said inner cylindrical sleeve has a plurality of elongated slots oriented perpendicular to said circumferential locking grooves; and said side wall on said outer cylindrical sleeve includes a plurality of elongated slots that are coaxially aligned with the slots formed on the side wall of the inner sleeve, whereby the aligned slots allow bone graft material to be placed within the inner and outer cylindrical sleeves which allows growth between existing bone and the implant to provide further stabilization.

3. The corpectomy device of claim 1, wherein the cylindrical shaped side wall of each sleeve includes a plurality of apertures to minimize the bone graft material and growth between existing bone and the implant.

4. The corpectomy device of claim 1, wherein a portion of said side wall on both said inner and outer cylindrical sleeve is solid allowing posterior placement and prevention of prevent bone migration toward the spinal cord.

5. The corpectomy device of claim 1, wherein said inner cylindrical member is configured to operatively engage a first end plate at said second end thereof, said outer cylindrical sleeve is configured to operatively engaged a second end plate at said second end thereof, wherein each of said end plates has a bone contacting surface configured and dimensioned to rest against a vertebra.

6. The corpectomy device of claim 5, wherein said first end plate is attached to said inner cylindrical sleeve with a base member having a raised outer edge so as to form a lip allowing acceptance of said first end plate.

7. The corpectomy device of claim 5, wherein said second end plate is attached to said outer cylindrical sleeve with a base member having a raised outer edge so as to form a lip allowing acceptance of said first end plate.

8. The corpectomy device of claim 1, wherein each of said locking pads being formed as fingers on the cylindrical side wall of said outer cylindrical sleeve and having relief portions at the base thereof, permitting them to pivot into the outer cylindrical sleeve, and, engagement teeth at an end opposite the base of said locking pad, said engagement teeth being formed on the inner surface of the locking pads.

9. The corpectomy device of claim 1, wherein the annular circumferential locking ring has an outer and an inner surface, the inner surface including locking pad relief surfaces, locking pad locking surfaces, and ramp surfaces located to allow movement of the locking ring from placement each of the locking pads within the locking pad relief surface to the locking pad locking surface thereby forcing the locking pads into a position engaging at least one of the circumferential locking grooves.

10. The corpectomy device of claim 1, wherein the outer cylindrical sleeve includes an aperture and a guide pin inserted therein, said guide pin is in operative engagement with a capture alignment slot formed in said inner cylindrical sleeve to maintain the inner sleeve in proper rotational alignment with said outer cylindrical sleeve.

11. The corpectomy device of claim 5, wherein the first and second end plates include snap in portions in the form of resilient fingers for attaching the first and second end plates into the bases of either the inner or outer cylindrical sleeve.

12. The corpectomy device of claim 11, wherein the angle between the snap in portion and the contacting surface can be varied to most any angle in both lordotic and kyphotic curves.

13. The corpectomy device of claim 5, wherein spikes are provided on the contacting surface of each of the endplates to provide secure positioning against the bone.

14. The corpectomy device of claim 5, wherein said inner cylindrical sleeve includes an aperture in the cylindrical side wall adjacent the second end to receive an alignment pin that cooperates with said first end plate.

15. The corpectomy device of claim 5, wherein said outer cylindrical sleeve includes an aperture in the cylindrical side wall adjacent the second end to receive an alignment pin that cooperates with said second end plate.

* * * * *